United States Patent

Wang et al.

[11] Patent Number: 5,573,990
[45] Date of Patent: Nov. 12, 1996

[54] PROCESS FOR THE CONVERSION OF METHANOL TO LIGHT OLEFINS AND CATALYST FOR SUCH PROCESS

[75] Inventors: Gongwei Wang; Muliang Ying; Xingchun Wang; Guoquan Chen, all of Dalian, China

[73] Assignee: Dalian Institute of Chemical Physics, Dalian, China

[21] Appl. No.: 287,677

[22] Filed: Aug. 9, 1994

Related U.S. Application Data

[62] Division of Ser. No. 54,591, Apr. 29, 1993, Pat. No. 5,367, 100.

[30] Foreign Application Priority Data

May 3, 1992 [CN] China ................... 92106213.3

[51] Int. Cl.⁶ ........................................ B01J 29/40
[52] U.S. Cl. .................................... 502/77; 502/65
[58] Field of Search .............................. 502/77, 65

[56] References Cited

U.S. PATENT DOCUMENTS 5,367,100 11/1994 Gongwei et al. ............... 585/640

*Primary Examiner*—Asok Pal
*Assistant Examiner*—Bekir L. Yildirim

[57] ABSTRACT

A zeolite catalyst from ZSM-5 modified with phosphorus, rare earth elements and pore structure regulator is used for methanol/dimethyl ether conversion to light olefins.

High temperature, non-recycling, continuous-running process is realized in the reactor system, comprising a dehydration reactor and several (2-n) adiabatic, fixed bed cracking reactors, loaded with the catalyst in multi-stage packing and operated in reaction regeneration cycles. The catalyst possesses high activity, high selectivity, good hydrothermal stability and long reaction life time.

Operation of 100% methanol conversion and >85% $C_2$–$C_4$ selectivity has been performed in a reactor system of the scale 0.7–1 ton $CH_3OH$/day for >600 hours on stream and with reaction time of single cycle >24 hours.

5 Claims, 6 Drawing Sheets

PROCESS FOR THE CONVERSION OF METHANOL TO LIGHT OLEFINS AND CATALYST FOR SUCH PROCESS

The application is a division of the application Ser. No. 08/054,591, filed Apr. 29, 1993, U.S. Pat. No. 5,367,100.

BACKGROUND OF THE INVENTION

The present invention relates to a process for obtaining light olefins from methanol and/or dimethyl ether (DME).

The catalytic conversion of methanol to hydrocarbons was first achieved by Mobil Oil Co. USA, over ZSM-5 zeolite catalyst in 1976, thereby a way of producing important raw materials, such as light olefins, from non-petroleum sources (coal and natural gas) was opened. This process is highly exothermic and the aimed product, light olefins, is further converted in the reaction zone. Consequently, the catalyst used was subjected to frequent regeneration and was easily damaged. Accordingly, various catalytic and engineering technologies have been explored with the purpose to control the reaction course, to enhance the selectivity for light olefins and to improve the stability of the catalyst. They include processes with different type of reactors, such as fixed or fluidized bed reactors, a process which yields a partial conversion at low temperature (<350° C.) with recycling, a process which yields a complete conversion at high temperature (>450° C.) without recycling, the reaction over different zeolite catalysts modified with various additives and also the reactions in the presence of some diluents in the feed.

In U.S. Pat. No. 4,035,430 a process for the production of gasoline range products from methanol over a ZSM-5 zeolite catalyst is disclosed. Methanol is catalytically converted to an ether rich product, and the latter is converted to aromatics and iso-paraffins. The exothermic temperature rise in the zeolite bed is kept low by mixing the ether-rich feed with a heat-dissipating material (hydrocarbon $C_1$–$C_5$, cooled methanol etc.).

In U.S. Pat. No. 4,542,252, a multi-stage fixed bed adiabatic reactor system for methanol conversion to light olefins is disclosed. Also in this case the methanol feed is first converted into an ether-rich equilibrium mixture in a catalytic dehydration reactor. Thereafter it is further converted in a catalytic cracking reactor so that the released reaction heat can be distributed over the two conversion reactors. Furthermore the zeolite catalyst in the cracking reactor is packed in several stages separately, and the reaction heat is removed directly or indirectly by coolant or cool feed passing through the interstage space in order to keep the inlet temperature and temperature rise of each bed stage substantially equal.

In U.S. Pat. Nos. 3,911,041, 4,049,573, 4,100,219 JP 60-126233, JP 61-97231, JP 62-70324 and EP 6501, the zeolite catalysts used for the conversion of methanol to olefins are chemically modified with phosphorus, magnesium, silicon and alkali metal elements to control the acidity. These catalysts are mostly used at moderate temperature in reaction-separation recycle process. The methanol conversion in a single cycle is only 15–50% and the duration of individual reaction cycle is not long.

SUMMARY OF THE INVENTION

The main object of the present invention is to provide an industrial process based on ZSM-5 modified catalyst for obtaining light olefins from methanol and/or DME. Another object is to provide a process for the preparation of a modified ZSM-5 catalyst which is adapted to be used in a process for the conversion of methanol to olefins. Another object is to provide a catalyst based on zeolite ZSM-5 which is particularly useful in the methanol conversion to olefins.

DETAILED DESCRIPTION OF THE INVENTION

Figure 1:
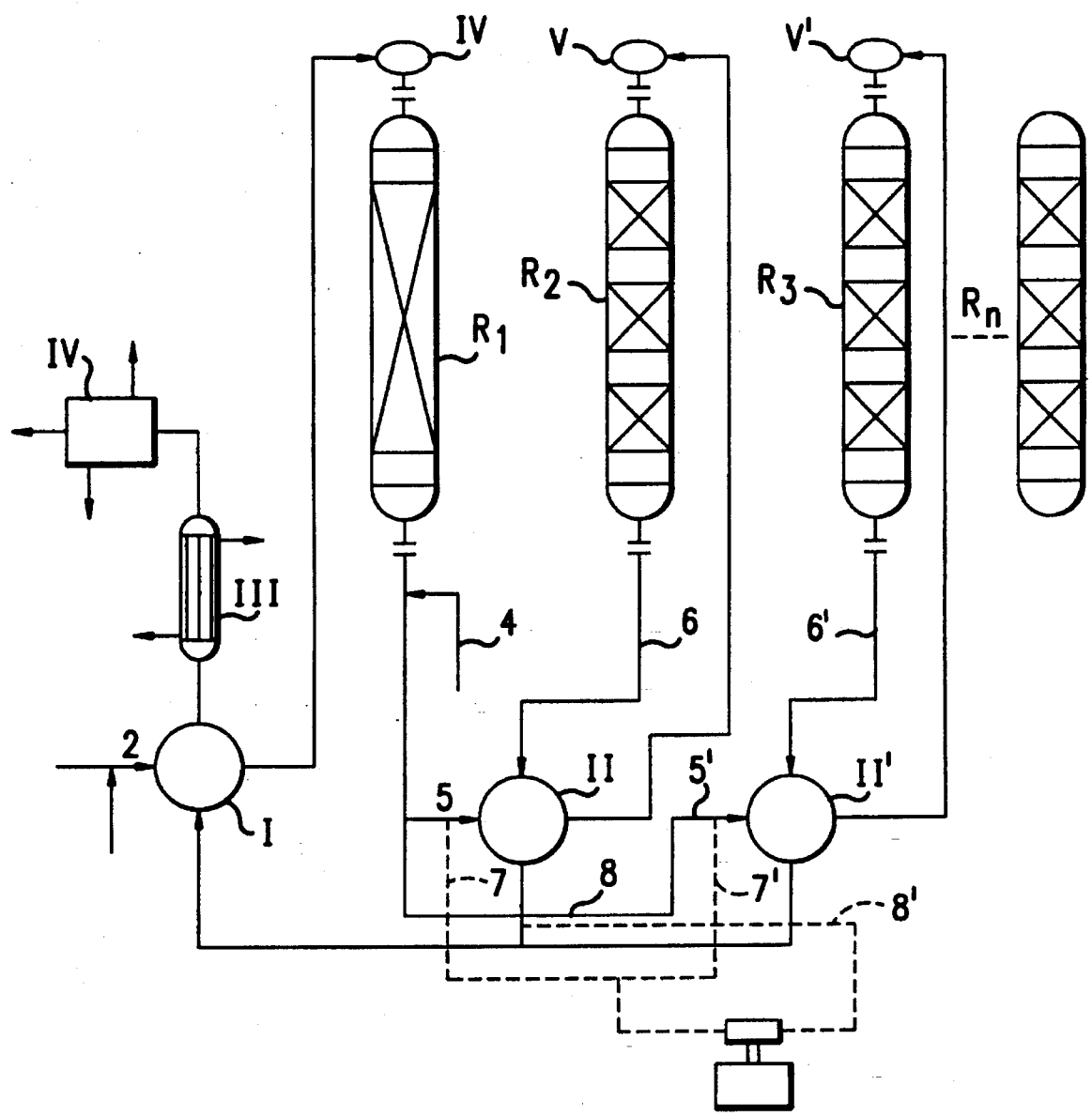
FIG. 1 is a schematic diagram of a multistage fixed bed reactor system for carrying out one embodiment of the conversion process of the invention.

In accordance with the present invention methanol and/or dimethylether is converted in presence of a catalyst which contains at least 0.7% by weight of phosphorus and at least 0.97% by weight of rare earth elements incorporated within the structure of the catalyst.

Preferably the amount of phosphorus is comprised between 0.7 and 5% by weight.

The phosphorus content in the catalyst is most preferably comprised between 1.3 and 1.7% by weight.

The rare earth elements incorporated with the crystal structure of the catalyst are preferably rich in lanthanum, the content of lanthanum in the catalyst being preferably comprised between 2.5 and 3.5% by weight.

The zeolite ZSM-5 based catalyst presents a mole ratio $SiO_2/Al_2O_3$ comprised between 40 and 80, a crystal size comprised between 1 and 10 µm and adsorption capacities of n-hexane and water 10–11% by weight and 6–7% by weight respectively.

The conversion process according to the present invention can be carried out on a large scale, realizing complete conversion of methanol/dimethyl ether without recycling, with high olefins yield and long duration time of single reaction operation (before regeneration). Moreover in the process according to the invention a big amount of water can be added to the starting materials before the conversion; water (about 16% by weight) is present in the raw methanol, water is injected to the feed of a dehydration reactor (upstream the conversion reactor) in order to control the temperature rising and steam is injected to the feed of the conversion reactor in order to maintain the $CH_3OH/H_2O$ weight ratio between 50/50 and 20/80, preferably at about 30/70. Notwithstanding such high amount of water, the catalyst according to the invention is not damaged under high temperature and hydrothermal conditions. After more than 530 hours of reaction, the crystallinity of catalyst determined by XRD analysis decreased only slightly, and loss of P and rare earths in the catalyst are very low according to the estimation of ESCA and chemical analysis respectively.

The active composition of the catalyst is a ZSM-5 zeolite modified by phosphorus and rare earth elements. Moreover a pore structure regulator is added during the kneading and moulding procedure. The incorporation of pore structure regulator (selected among starch, active carbon, carboxymethylcellulose and powder obtained from the milling of Sesbania seeds) improves the pore size distribution of the catalyst and further promotes its stability. With the incorporation of the above pore structure regulator a bimodal pore size distribution at 35–45 Å and 170–250 Å in the final catalyst is obtained, which is deemed to be responsible for the good hydrothermal stability and high selectivity of the catalyst itself towards light olefins.

Preferably the catalyst presents a pore size distribution at about 40 Å and 177 Å.

The presence of rare earth elements, preferably in an amount comprised between 0.97 and 6.5 by weight in the modified catalyst, enhances the hydrothermal stability of zeolite at high temperature. The zeolite is preferably mixed with a binder, preferably $SiO_2$, and the ratio zeolite/$SiO_2$ is preferably comprised between 40/60 and 70/30 by weight.

The catalyst according to the present invention is prepared according to the following general procedure.

1. Synthesis of Zeolite ZSM-5

The aqueous solution of sodium silicate, aluminium sulphate, sodium hydroxide and tetra-propyl ammonium (TPA) compound are mixed together and gel forms in a stainless steel autoclave. Crystallization is performed at 150°–200° C. over 12–96 hours. Thereafter the autoclave is cooled and the crystallized product is filtered and washed with deionized water to pH-7. After drying at 110°–120° C., zeolite ZSM-5 was obtained. $SiO_2/Al_2O_3$ ratio of the zeolite is in the range 40–80 and the crystal size is in the range 1–10 μm. The adsorption capacities of n-hexane and water on ZSM-5 are 10–11% (weight) and 6–7% (weight) respectively.

According to the same above procedure, a zeolite ZSM-5 may also be prepared by substituting hexamethylenediamine (HDA) for TPA used as template in catalyst preparation. The use of HDA reduces the cost of the catalyst in comparison with that prepared by using TPA. Moreover X-ray diffraction analysis indicates the identity of framework topology between TPA and HDA ZSM-5 zeolites.

2. Kneading and Moulding

The zeolite powder as prepared above is first mixed with silica sol (binder) in the following proportion: zeolite/$SiO_2$= 40/60–70/30(weight), preferably 65/35 (wt). A pore structure regulator, as specified above, amounting to 3–10% (wt), preferably 5–8%(wt) of said mixture is then incorporated into it. The resulting mixture is kneaded and extruded into cylindrical pellets (φ2×8 mm). After drying at 110° C. for 10–20 hours, the catalyst is calcined at 540° C., first in inert atmosphere and then in air, for more than 10 hours.

3. Chemical Modification

(1) Ion Exchange with Hydrochloric Acid

The cylindrical zeolite particle prepared according to the above step (2) is treated with hydrochloric acid, preferably 0,5N, for hydrogen exchange under the following conditions: HCl solution (ml)/zeolite particles (g)=10–30 ml/g, preferably 10–15 ml/g; exchange temperature 70°–90° C.; exchanging 4 times, each time for 2–3 hours. Then it is washed with deionized water until no Cl⁻ is detected. The product is filtered and dried at about 110° C. for 3–5 hours. After calcination at about 540° C. for about 3 hours, the product zeolite HZSM-5 is obtained, the sodium content of which is<0.05%(by weight).

(2) Impregnation with Phosphoric Acid

The zeolite HZSM-5 prepared as described above is impregnated in aqueous phosphoric acid solution under reduced pressure preferably comprised between 0.08 and 0.09 MPa for 2–3 hours. It is dried at<110° C. for 3–5 hours and calcined at about 540° C. for about 3 hours, the phosphorus content of the obtained product PZSM-5 being 0.7–5%(by weight).

(3) Impregnation with Salt Solution of Rare Earth Elements

The zeolite PZSM-5 as prepared above is further impregnated in aqueous solution of lanthanum salt or mixed rare earth salts rich in lanthanum. Impregnation is conducted under reduced pressure comprised preferably between 0.08 and 0.09 Mpa for 2–3 hours. After drying at<110° C. for 3–5 hours and calcination at about 540° C. for 3 hours, the product zeolite catalyst P-Re(La)-ZSM-5 is obtained. The content of rare earth elements in the composite product amounts preferably to 0.97–6.5%(by weight).

(4) Hydrothermal Treatment at High Temperature

The zeolite catalyst P-Re(La)-ZSM-5 obtained as described above is finally treated for 3–10 hours in hydrothermal condition: water/catalyst=1–20 ml/g; temperature 500°–600° C. After calcining once more at about 540° C. for about 3 hours, the zeolite modified catalyst is ready to be used in the catalytic reaction of methanol conversion to light olefins.

In the enclosed FIG. 1 a schematic view is shown of the technology of multistage fixed bed reactor system in which an alternating reaction-regeneration switching operation is provided. The system comprises a dehydration reactor $R_1$ and the multi-stage fixed bed adiabatic reactor $R_2$, $R_3$, . . . $R_n$. equipped with interstage cooling devices.

The feed stock methanol containing 0–80% (by weight) of water is fed along the line 2 and passes through the heat exchanger I and the preheater IV, where it is heated to about 350° C. It is converted into an equilibrium mixture of methanol-DME-$H_2O$ in the dehydration reactor, operating at 300°–400° C., 0.01–0.04 MPa (gauge) and weight hourly space velocity (WHSV) 1–1.5 hr⁻¹. The effluent from $R_1$, after being adjusted to the composition of methanol/water= 10–50/90-50 by mixing with the superheated water vapour from line 4, is fed along line 5 and is heated to 480° C. in heat exchanger II and preheater V.

The composite gas is fed into the cracking reactor $R_2$, operating under the following conditions: temperature 400°–600° C., preferably 500°–550° C.; pressure 0.01–0.04 MPa and weight hourly space velocity 0.5–10 hr⁻¹, preferably 1–5.4 hr⁻¹. The cracking effluent (methanol conversion=100% and $C_2^=$–$C_4^=$ selectivity>85%) runs along line 6, passes through the heat exchanger II and I and a cooler III and goes to the product separating unit VI. The reaction products are separated into the gas phase rich in light olefins and water with a small amount of hydrocarbons heavier than $C_6$.

When the methanol appears at the outlet of the cracking reactor $R_2$ or the $C_2^=$–$C_4^=$ selectivity in the cracking product becomes<85%, the reactor $R_2$ is disconnected from the operating system. In place of $R_2$, the reactor $R_3$, having been regenerated and ready for reaction, is reconnected to the system. The reactor $R_3$ is operated under the same conditions along the corresponding lines as the previous reactor $R_2$, the switched off reactor $R_2$ being regenerated. Accordingly, nitrogen gas, conducted along line 7 and through heat exchanger II and preheater V, is introduced into the reactor $R_2$ and fed out along line 6, through exchanger II and along line 8. The system is purged until the hydrocarbon content in the blow-out gas becomes<0.2%. Then air is allowed to diffuse into the purging gas while keeping the oxygen content in the outlet gas from reactor $R_2$<3–5%. Air concentration is raised gradually until $CO_2$ content of the outlet gas from $R_2$ is<1%.

Thereafter, the regeneration continues for about 4 hours at about 550° C. with air cycle only. The whole reaction system runs continuously while the reactors $R_2, R_3, \ldots R_n$ undergo reaction-regeneration alternately.

The catalyst according to the present invention is distinct in its high activity of methanol/DME conversion and high selectivity for light olefins. It possesses especially high hydrothermal stability. The catalyst has been utilized in a pilot plant of the scale of 0.7–1 ton methanol per day operated according to the technology provided in the invention, i.e. 500°–550° C., 0.01–0.04 MPa (gauge) and WHSV 1.0 $hr^{-1}$. The methanol conversion attains 100%, needing no separation and recycling to the feed, and the $C_2^=$–$C_4^=$ yield is>85%. The operation continues for more than 600 hours on stream and the single reaction cycle is longer than 24 hours.

The following examples illustrate the preparation of the catalyst of the present invention more specifically. In the examples the amount of the modifiers is expressed as % by weight.

EXAMPLE 1

100 g of the zeolite powder ZSM-5$_{TPA}$ ($SiO_2/Al_2O_3$=61, crystal size 2–5 μm, adsorption capacities of n-hexane and water 11.2 and 7.0% by weight respectively) were mixed with 103.7 g silica sol ($SiO_2$ content 40.8% by weight). 6 ml of saturated ammonium nitrate solution was added dropwise. After being kneaded homogeneously, the mixture was extruded into cylindrical pellets (φ 2×8 mm). The zeolite particles were dried for 10 hours below 110° C. and calcined at 540° C., first for 3 hours in $N_2$ atmosphere and then for another 3 hours in air. The baked cylindrical particles were treated with 0.5N HCl solution for hydrogen exchange. HCl solution was added to the zeolite in the ratio 15 ml HCl/g zeolite. Ion exchange was carried out at 85° C. for 2 hours. The same procedure of hydrogen exchange was repeated four times. Then, the treated zeolite was washed with deionized water until no $Cl^-$ was detected, filtered, dried at 120° C. for 3 hours and calcined at 540° C. for 3 hours. The product HZSM-5 was obtained, sodium content of which was less than 0.05%. 20 g of the above zeolite HZSM-5 was impregnated in 30 g aqueous solution of 12.8%(weight) of phosphoric acid under reduced pressure and at temperature of 80° C. for 2 hours. After drying at 110° C. for 3 hours and calcining at 540° C. for 3 hours, a zeolite catalyst PZSM-5 was obtained. The zeolite catalyst P-ZSM-5 was further impregnated in 23 g aqueous solution of 17.2% (by weight) $La(NO_3)_3$ under reduced pressure and at the same conditions as the foregoing phosphorus impregnation. After drying and calcination the product obtained was P-La-ZSM-5.

Finally, the zeolite catalyst P-La-ZSM-5 was subjected to a hydrothermal treatment in a tubular furnace at 550° C., into which water was fed for one hour at the rate of 1.0 ml water/g cat. hr. Thereafter, the catalyst was calcined once more in air at 540° C. for 3 hours. The catalyst contained 1.41% P and 3.0% La. The results of methanol conversion to light olefins of such catalyst used in a laboratory reactor are shown in Table 1 enclosed. In Table 1 it can be seen that the catalyst according to the invention possesses high capability for methanol conversion and light olefins formation.

Figure 2:
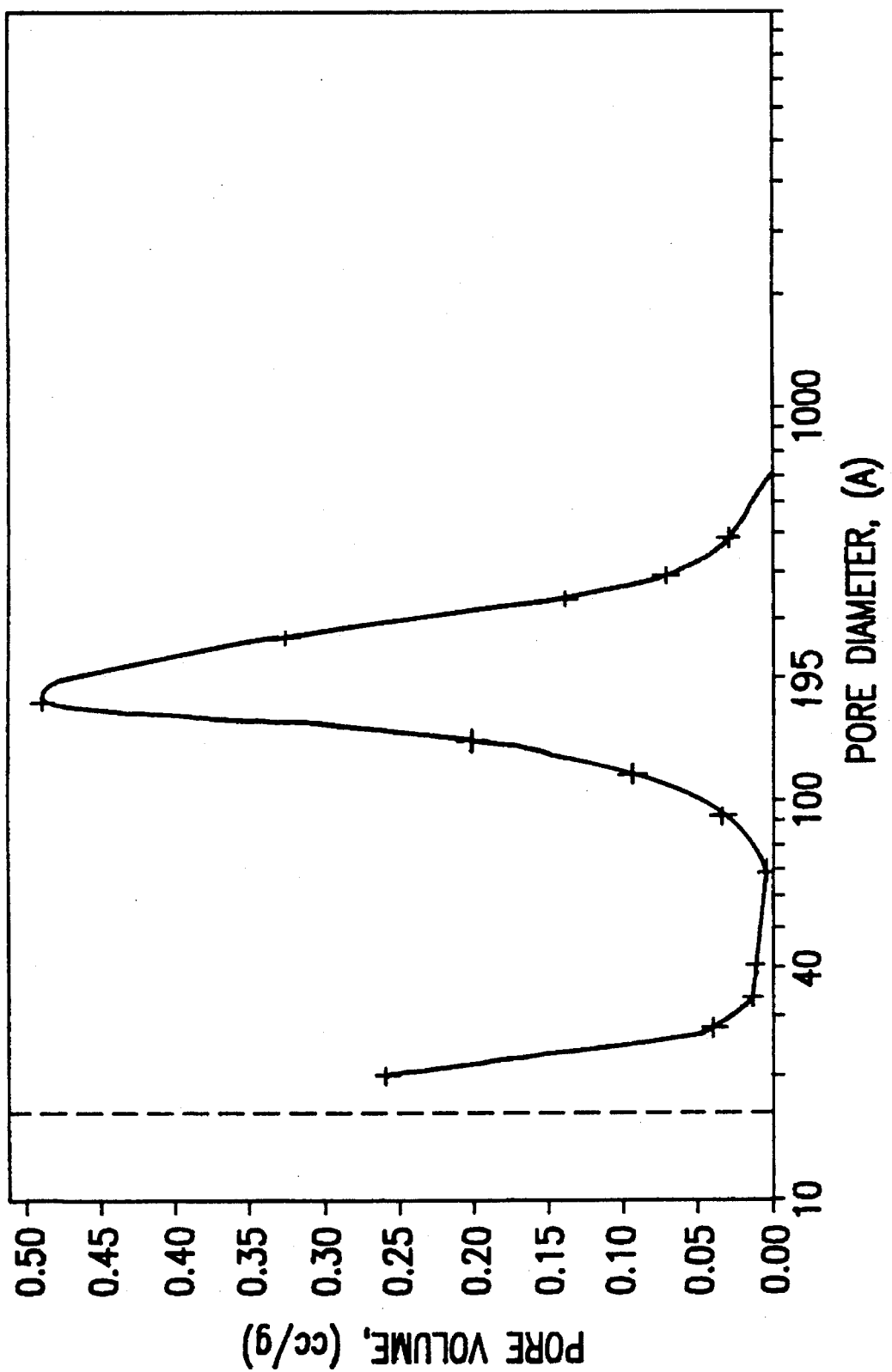
FIG. 2 is a plot of the pore size distribution of a specific embodiment of the catalyst of this invention made without a pore structure regulator according to Example 1 hereinafter set forth.

Data on pore size structure of the catalyst were obtained by using ASAP 2400 type adsorption meter (Micrometrics Instrument Corporation-USA). The pore size distribution is shown in the enclosed FIG. 2. In the condition of $N_2$ adsorption, the lower limit for the determination of the pore diameter is about 20 Å. The pore size distribution shows a peak at about 195 Å.

EXAMPLE 2

Onto 100 g of the same zeolite powder ZSM-5$_{TPA}$ used in Example 1, 10.2 g of Sesbania (Tian-qing-fen) seeds powder and 103.7 g silica sol ($SiO_2$ content 40.8% by weight) were incorporated. 6 ml saturated ammonium nitrate solution was added and the mixture was kneaded homogeneously and extruded into cylindrical pellets (φ2×8 mm). Thereafter the same procedure as described in Example 1 was carried out. The end product zeolite catalyst P-La-ZSM-5 was obtained. Catalysts of Example 1 and 2 were tested for methanol conversion reaction in a laboratory fixed bed reactor with continuous feeding. The reaction conditions were the following: temperature 550° C.; feed composition MEOH/$H_2O$ =30/70(weight); WHSV 1.5 $hr^{-1}$. When the methanol appeared in the liquid phase of the effluent, feeding was interrupted. After regeneration the catalyst was ready to be used in the next reaction cycle. Reaction of three cycles were carried out over both catalysts. The results are listed in Table 2. The durations of the first reaction cycle in both catalysts are similar. In the second and third cycles, the reaction time of Example 2 with Sesbania powder (Tian-qing-fen) is evidently longer then that of Example 1. During the three reaction periods high selectivity of light olefins ($C_2^=$–$C_4^=$) is achieved on both catalysts, i.e. 83.80–86.07% (by weight) for Example 1 and 85.57–87.26% (by weight) for Example 2.

Figure 3:
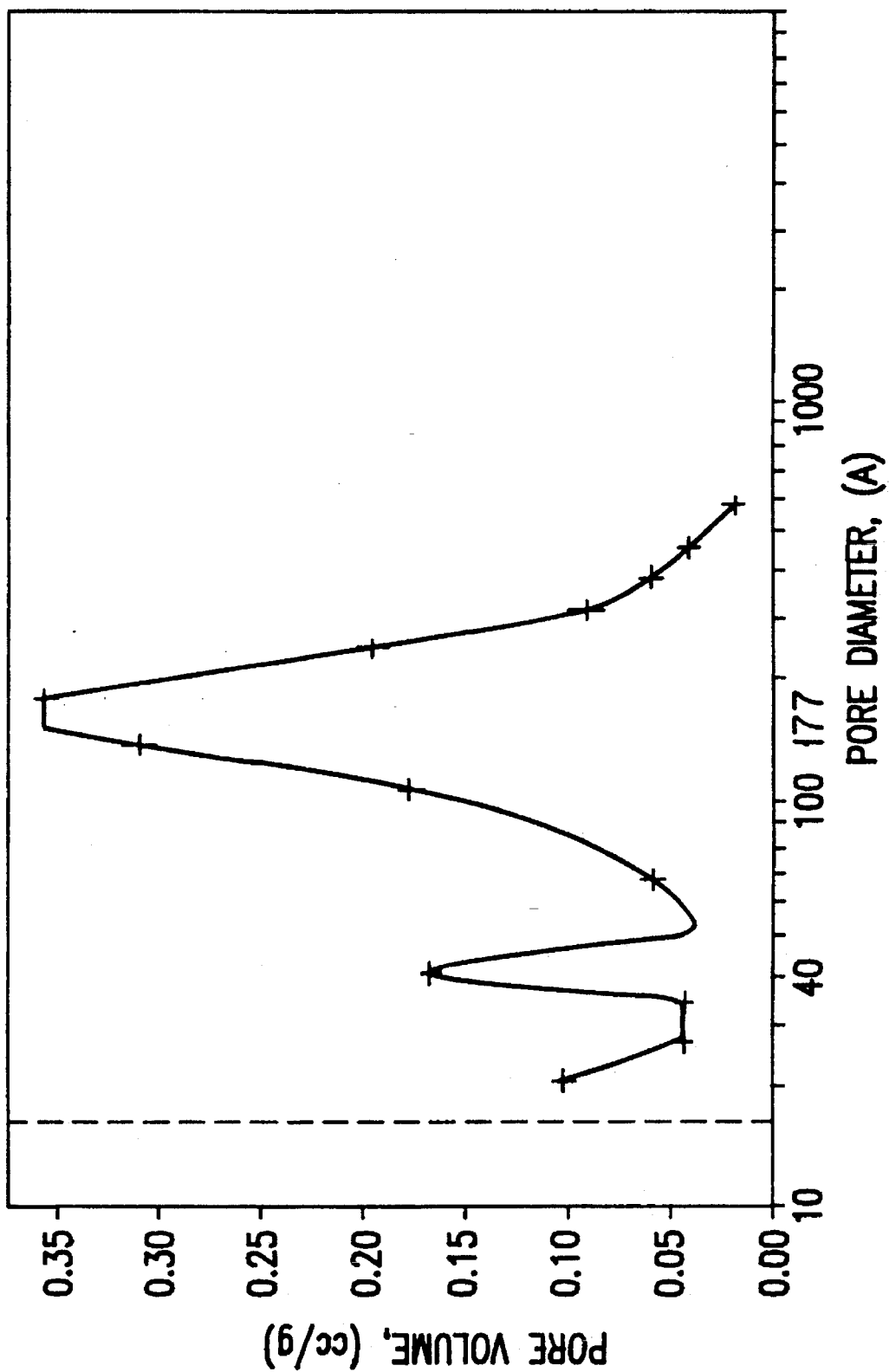
FIGS. 3–6 are plots of the pore size distribution of specific embodiments of the catalyst of this invention made with the pore structure regulators of Examples 2–5 which appear hereinafter.

The pore size distribution of the catalyst according to Example 2 is shown in the enclosed FIG. 3. It is clear that the catalyst obtained by using the Sesbania seeds powder presents a bimodal pore size distribution, with two peaks at 40 and 177 Å.

EXAMPLE 3

Figure 4:
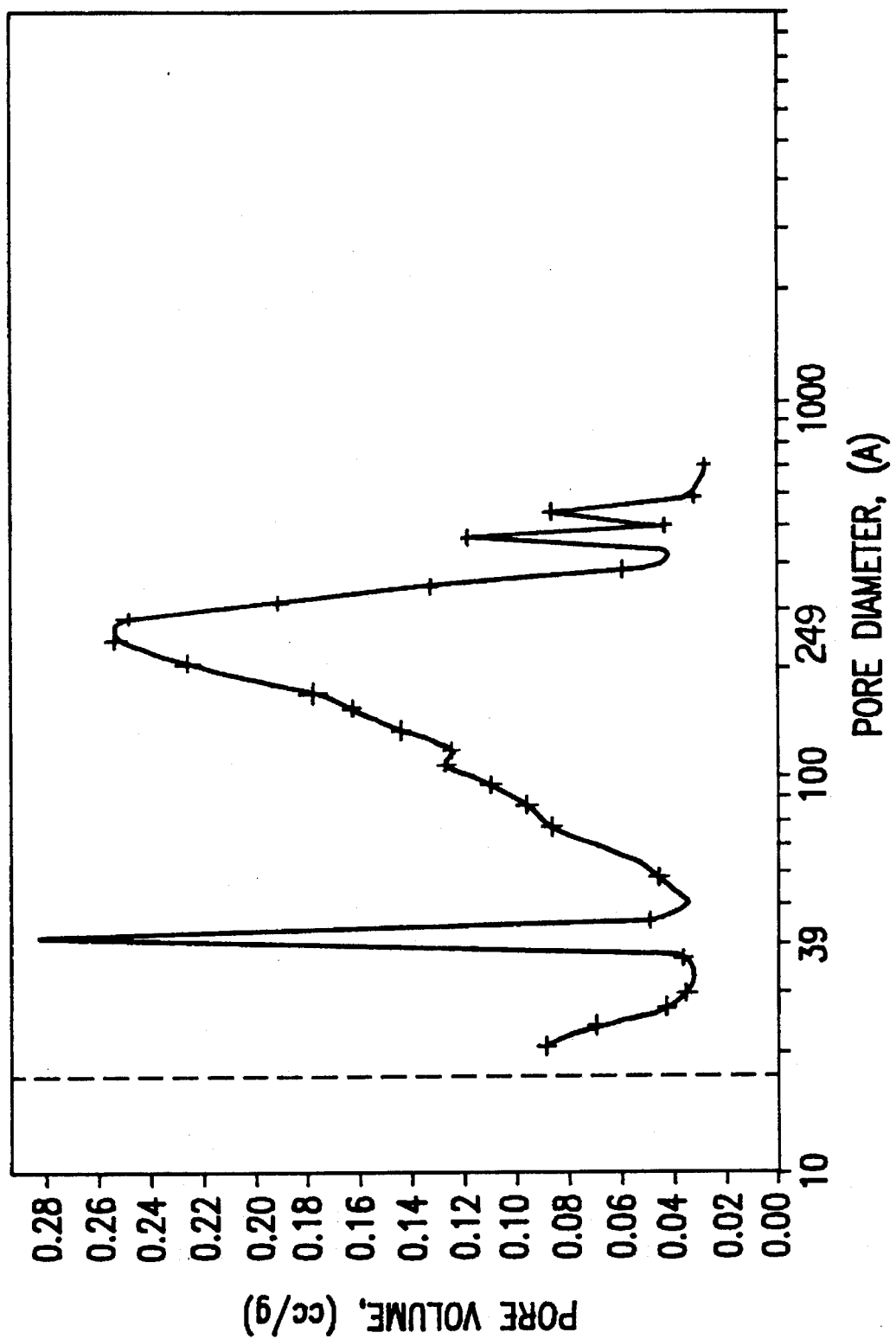

A ZSM-5 based catalyst has been prepared according to the same procedure of Example 2 above, using the same amount of carboxymethylcellulose as pore structure regulator instead of Sesbania seed powder. The pore size distribution of such catalyst is shown in the enclosed FIG. 4. The bimodal pore size distribution shows two main peaks at 39 and 249 Å respectively.

EXAMPLE 4

Figure 5:
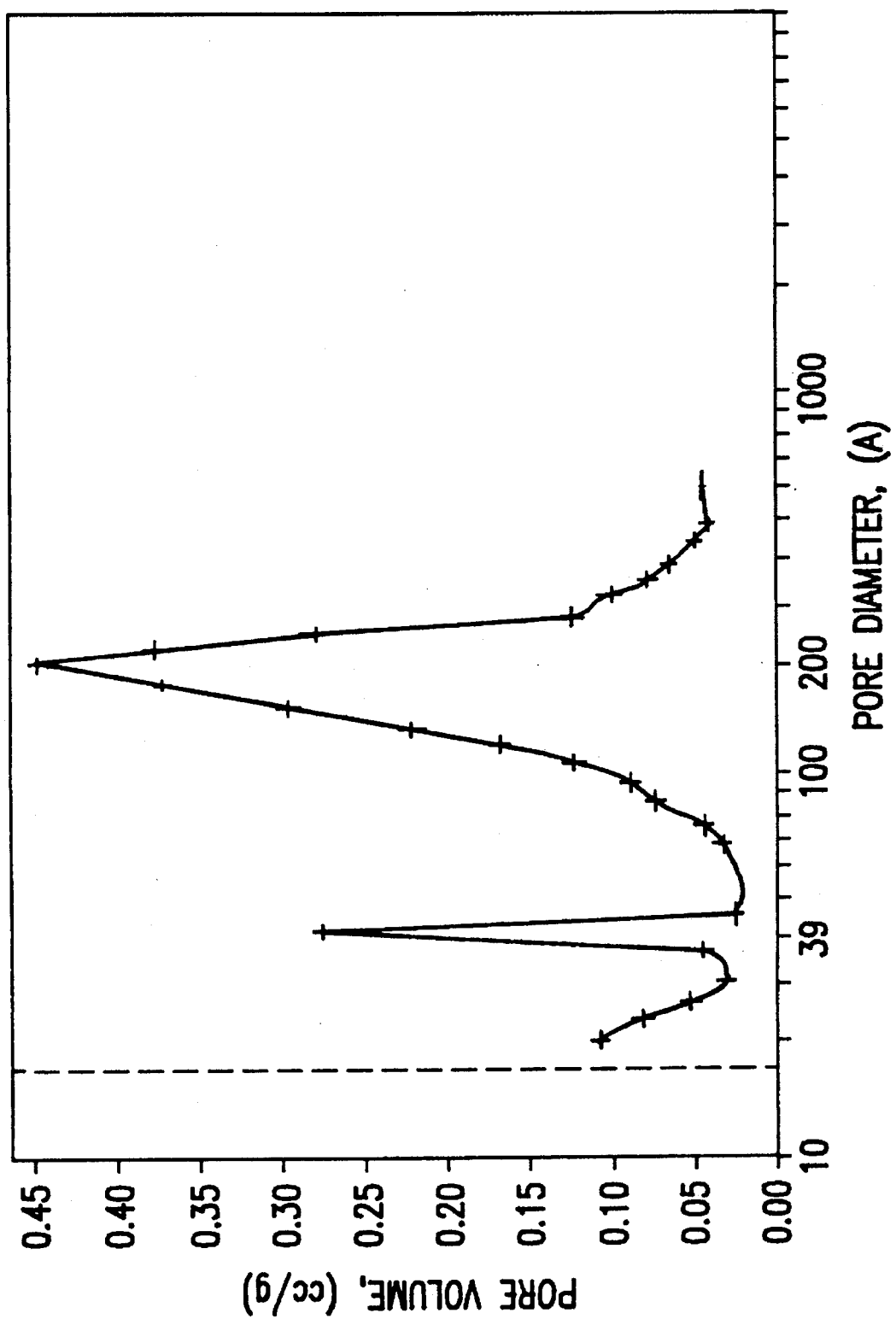

A ZSM-5 based catalyst has been prepared according to the same procedure of Example 2 above, using activated carbon as pore structure regulator instead of Sesbania seed powder. The pore size distribution of such catalyst is shown in the enclosed FIG. 5. The bimodal pore size distribution shows two main peaks at 39 and 200 Å respectively.

EXAMPLE 5

Figure 6:
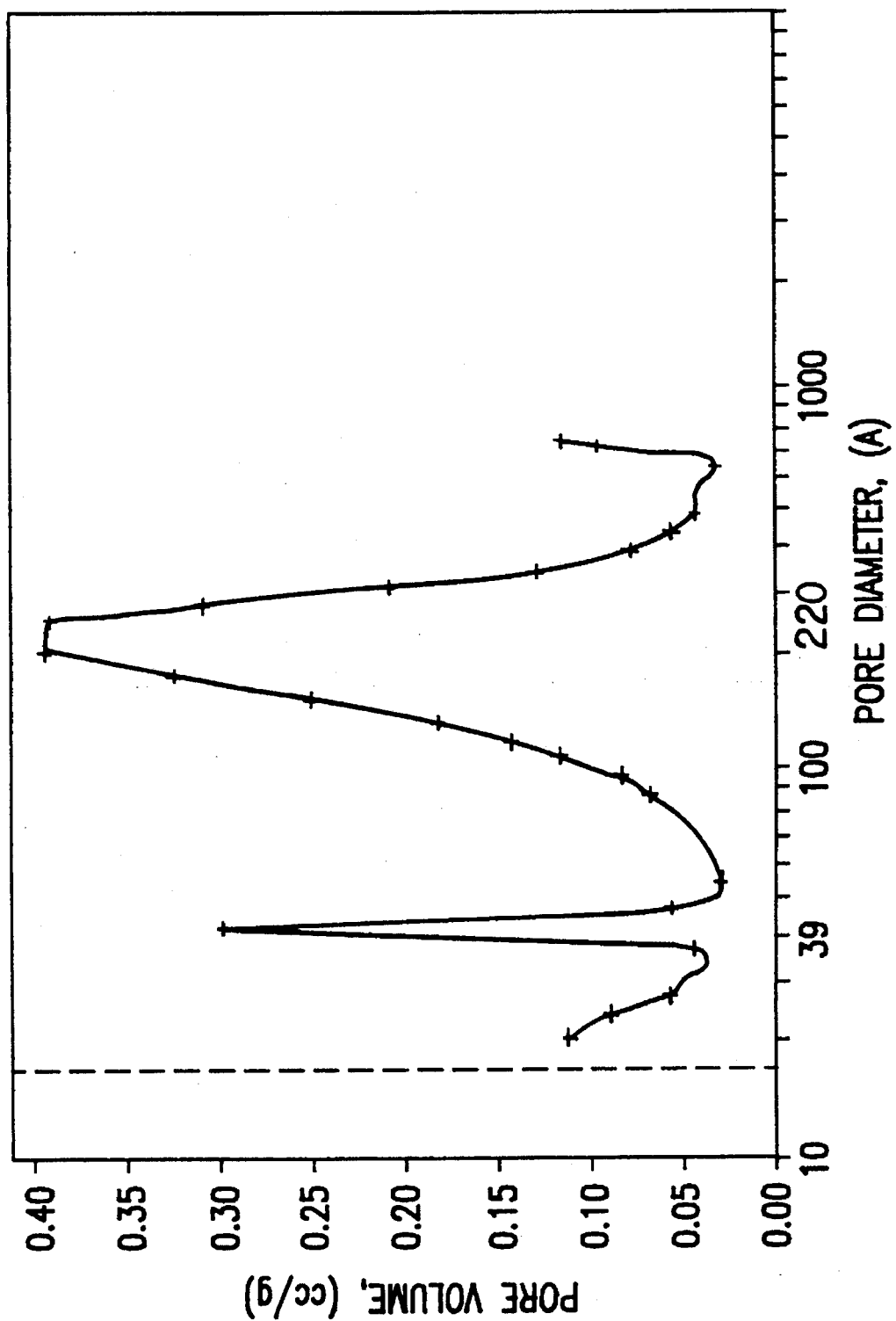

A ZSM-5 based catalyst has been prepared according to the same procedure of Example 2 above, using starch as pore structure regulator instead of Sesbania seed powder. The pore size distribution of such catalyst is shown in the enclosed FIG. 6. The bimodal pore size distribution shows two main peaks at 39 and 220 Å respectively.

The thermal stability of the catalysts prepared according to the above examples 3–5 was slightly lower than the stability of the catalyst prepared according to Example 2, but always higher than the stability of the catalyst according to example 1.

EXAMPLE 6 (comparison)

To 43 g of zeolite powder ZSM-5$_{TPA}$ (SiO$_2$/Al$_2$O$_a$=50.2, crystal size 4–7 µm, adsorption capacities of n-hexane and water 10.5% and 6.3% by weight respectively) 41.8 g silica sol (SiO$_2$ content 40.8 by weight) were added. The mixture was kneaded with 3 ml of saturated ammonium nitrate solution and extruded to cylindrical pellets (φ 2×8 mm). After being dried at 110° C. for 3 hours, the zeolite was calcined at 540° C. in N$_2$ atmosphere for 3 hours and in air for another 3 hours. The baked zeolite was ion exchanged repeatedly four times, each time with 600 ml of 0.5N HCl at 85° C. for 2 hours. It was washed with deionized water until no Cl$^-$ was detected, filtered, dried at 110° C. for 3 hours and calcined in air at 540° C. for 3 hour. The zeolite obtained was HZSM-5.

30 g of the above prepared zeolite HZSM-5 was impregnated with 50.2 g aqueous solution of 12.4% (by weight) phosphoric acid under 0.088 MPa and at a temperature of 80° C. for 2 hours. Then it was filtered, dried at 110° C. for 3 hours and calcined at 540° C. for 3 hours. Further, it was treated by water vapour at 550° C. for 2 hours. A phosphorus-modified zeolite catalyst PZSM-5 was obtained, which contained 1.58% P.

EXAMPLE 7

30 g of the catalyst prepared as described in Example 6 (without the final treatment with water vapour) was impregnated for 2 hours in 32 g of aqueous solution of 16.8% (by weight) La(NO$_3$)$_3$ under reduced pressure of 0.09 MPa and at a temperature of 80° C. After filtration, the product was dried at 110° C. for 2 hours, calcined at 540° C. for 3 hours and treated with water vapour at 550° C. for 2 hours. The zeolite catalyst obtained was P-La-ZSM-5. It contained 1.43% P and 2.87% La. Such catalyst P-La-ZSM-5 was compared with PZSM-5 in Example 3 for their catalytic properties of methanol conversion. The laboratory reaction condition used were as follows: temperature 550° C., WHSV 4.6–5.4 hr$^{-1}$, and feed composition MEOH/H$_2$O= 30/70. The results are reported in Table 3 and show that the incorporation of rare earth element (La) into PZSM-5 increases the reaction time on stream (before the catalyst needs to be regenerated) from 126 hours to 188 hours, while the overall selectivity for olefins remains little changed.

EXAMPLE 8

When the phosphoric acid of 12.8% (by weight) used in Example 2 was substituted by an aqueous solution of 4.3% (by weight) phosphoric acid and other procedures and conditions were the same, the P content of the end product obtained was 0.64%. This catalyst was tested for methanol conversion MEOH/H$_2$O=30/70. The selectivity of light olefins remains at 85.8% but the methanol conversion become lower. i.e. 98.2%.

EXAMPLE 9

The same procedure and conditions described in Example 2 were repeated but an aqueous solution of 44.5% (by weight) La(NO$_3$)$_3$ was used to substitute the 17.2% (by weight) La(NO$_3$)$_3$ solution. An end product zeolite catalyst was prepared with a La content of 6.48%.

It was tested for methanol conversion in the same reaction condition of Example 8. The methanol conversion was 100% and C$_2^=$–C$_4^=$ selectivity was 86.8%.

EXAMPLE 10

The same procedure and conditions described in Example 2 were repeated but 20.5 g of Sesbania (Tian quing-fen) seeds powder were used instead of 10.2 g. An end catalyst P-La-ZSM-5 was obtained which was tested in the same reaction condition of methanol conversion as in Example 2. The methanol conversion was found to be 100% and C$_2^=$–C$_4^=$ selectivity 88.3%.

EXAMPLE 11

A catalyst was prepared according to the same procedure of Example 2 but 339.8 g of silica sol (SiO$_2$ 40.8% by weight) was used instead of 103.7 g giving the ratio zeolite/SiO$_2$ of 40/60. The catalytic behaviour of the end catalyst was a methanol conversion 100%(weight) and a C$_2^=$–C$_4^=$ selectivity 87.2%(weight).

EXAMPLE 12

Tests on high selectivity (C$_2^=$ 27–32%, C$_3^=$ 36–41%, C$_4^=$ 15–17% (by weight) and long operation time (single reaction period 24 hours and accumulative period>500 hours) of methanol conversion reaction have been carried out in a pilot plant loaded with the catalyst prepared according to Example 1.

Two portions of catalyst were loaded in the cracking reactors R$_2$ and R$_3$ (see FIG. 1). In each of them 29.9 Kg. catalyst was packed, separated into three equal-weight section. Methanol conversion reaction was operated according to the reaction-regeneration switching process as described above. The reaction condition was 500°–550° C., 0.01–0.04 MPa (gauge) and WHSV of methanol 1.0 hr$^{-1}$. The operating performance of the second, the ninth and the sixteen switching cycles are given in Table 4. It shows that the catalyst possesses high methanol/DME conversion activity and good light olefins selectivity. The superior character is unaffected by the reaction-regeneration operation, the catalyst remains stable even after sixteen reaction-regeneration cycles and 630 hours on stream operation. These results reveal not only the high stability of the provided catalyst but also the advantage of the technology of reaction-regeneration switching operation described in the present invention.

EXAMPLE 13

Example 1 was repeated starting from a zeolite powder HDA ZSM-5 prepared by using HDA as template agent. The tests on the pilot plant were carried out according to the same procedure of Example 12. The results are reported in Table 5.

TABLE 1

| Accumulative operation time (hr) | | 60 | 120 | 180 | 240 | 300 | 360 | 420 | 480 | 500 |
|---|---|---|---|---|---|---|---|---|---|---|
| Conversion of methanol % (wt) | | 100 | 100 | 100 | 100 | 100 | 100 | 100 | 100 | 100 |
| HC yield % (wt) | | 98.41 | 98.89 | 99.19 | 97.46 | 96.28 | 97.46 | 99.17 | 98.56 | 98.39 |
| Distribution of HC products in gaseous phase % (wt) | $C1°$ | 2.11 | 2.88 | 2.16 | 3.50 | 2.99 | 2.98 | 2.87 | 3.24 | 2.46 |
| | $C2^-$ | 30.69 | 29.01 | 29.30 | 27.17 | 28.95 | 30.64 | 31.63 | 30.29 | 32.94 |
| | $C3^-$ | 39.33 | 41.58 | 41.08 | 41.64 | 39.30 | 39.29 | 38.27 | 38.82 | 36.50 |
| | $C4^-$ | 17.39 | 17.37 | 17.86 | 17.12 | 16.43 | 15.69 | 16.93 | 17.60 | 16.32 |
| | $C2°-C4°$ | 3.30 | 1.18 | 1.33 | 1.04 | 1.44 | 1.75 | 1.63 | 1.58 | 2.65 |
| | $C6^+$ | 1.92 | 3.83 | 4.46 | 5.08 | 4.80 | 3.89 | 4.72 | 6.14 | 3.31 |
| | $C2^--C4^-$ | 87.41 | 87.96 | 88.24 | 85.96 | 84.69 | 85.60 | 86.65 | 86.41 | 85.58 |

Reaction time of single cycle >24 hours; WHSV (MEOH): 0.7–1.0 $hr^{-1}$; MEOH/$H_2O$ = 30/70; Temp.: 490–550° C.; Pressure: 0.04–0.05 MPa.

TABLE 2

| Catalyst | | Ex. 1 | | | Ex. 2 | | |
|---|---|---|---|---|---|---|---|
| Operation cycle | | 1 | 2 | 3 | 1 | 2 | 3 |
| MEOH conversion % | | 100 | 100 | 100 | 100 | 100 | 100 |
| Reaction time (hr) | | 15 | 12 | 9 | 14 | 18 | 18 |
| Distribution of products in gaseous phase % (wt) | CO | 1.80 | 2.84 | 2.58 | 2.32 | 2.51 | 2.29 |
| | $CH_4$ | 4.32 | 4.50 | 4.66 | 3.24 | 3.23 | 3.27 |
| | $C2^-$ | 24.66 | 24.57 | 24.08 | 27.25 | 25.82 | 25.60 |
| | $C3^-$ | 45.87 | 44.29 | 43.65 | 44.56 | 45.73 | 43.83 |
| | $C4^-$ | 15.56 | 15.85 | 16.07 | 14.87 | 15.71 | 16.14 |
| | $C2^--C4^-$ | 86.07 | 84.71 | 83.80 | 86.68 | 87.26 | 85.57 |

TABLE 3

| Type of catalyst | | PZSM-5 | P—La—ZSM-5 |
|---|---|---|---|
| Reaction time (hr) | | 126 | 188 |
| MEOH conversion % (wt) | | 100 | 100 |
| HC yield % (wt) | | 99.5 | 99.4 |
| Selectivity of light olefins % (wt) | $C2^-$ | 27.9 | 33.3 |
| | $C3^-$ | 41.9 | 39.9 |
| | $C4^-$ | 16.9 | 11.9 |
| | $C2^--C4^-$ | 86.7 | 85.1 |

TABLE 4

| Cycle number | | 2 | | | | | 9 | | | | | 16 | | | | |
|---|---|---|---|---|---|---|---|---|---|---|---|---|---|---|---|---|
| reaction time (hr) * | | 5 | 10 | 15 | 20 | 25 | 5 | 10 | 15 | 20 | 25 | 5 | 10 | 15 | 20 | 25 |
| Accumulative operation time (hr) | | 45 | 50 | 55 | 80 | 65 | 375 | 380 | 385 | 390 | 395 | 610 | 615 | 620 | 625 | 630 |
| Distribution of products in gaseous phase % (wt) | $C1°$ | 2.01 | 1.95 | 2.21 | 3.12 | 1.52 | 1.56 | 1.71 | 1.98 | 2.41 | 2.93 | 1.86 | 2.12 | 1.63 | 1.96 | 2.61 |
| | $C2^-$ | 31.05 | 31.70 | 31.33 | 28.93 | 28.26 | 31.51 | 32.19 | 32.06 | 32.30 | 31.39 | 33.46 | 34.46 | 31.16 | 30.29 | 30.75 |
| | $C3^-$ | 41.79 | 41.01 | 42.26 | 41.98 | 39.72 | 37.91 | 39.10 | 39.71 | 39.53 | 39.25 | 36.82 | 38.33 | 38.95 | 39.16 | 38.85 |
| | $C4^-$ | 18.81 | 16.52 | 15.94 | 16.12 | 20.38 | 16.79 | 16.09 | 15.95 | 15.57 | 15.06 | 15.99 | 14.46 | 16.91 | 17.10 | 16.68 |
| | $C2°-C4°$ | 2.08 | 2.03 | 1.87 | 1.37 | 2.02 | 2.30 | 1.73 | 1.37 | 1.11 | 0.99 | 3.04 | 1.98 | 1.46 | 1.23 | 1.03 |
| | $C5^+$ | 0 | 1.86 | 1.43 | 1.25 | 4.14 | 4.38 | 3.77 | 3.51 | 4.68 | 5.29 | 3.53 | 2.58 | 5.46 | 6.41 | 6.44 |
| $C2^--C4^-$ yield % (wt) | | 89.04 | 89.21 | 89.53 | 89.01 | 88.38 | 86.22 | 87.24 | 87.81 | 87.42 | 86.70 | 86.10 | 88.37 | 86.65 | 85.89 | 88.29 |
| MEOH conversion % (wt) | | 100 | 100 | 100 | 100 | 100 | 100 | 100 | 100 | 100 | 100 | 100 | 100 | 100 | 100 | 100 |

* Data collected before 25 hours of reaction time in every operation cycle.

TABLE 5

Pilot Reaction Results of ZSM-5 Zeolite Synthesized in The Presence of HDA

| Time on stream (hr) | | 40 | 45 | 50 | 55 | 60 | 65 | 85 |
|---|---|---|---|---|---|---|---|---|
| MEOH Conv. % | | 100 | 100 | 100 | 100 | 100 | 100 | 100 |
| $C2^--C4^-$ Selc. % | | 85.21 | 87.09 | 88.49 | 88.27 | 85.07 | 85.27 | 85.63 |
| Products distribution of gaseous phase % | $C1°$ | 4.04 | 4.35 | 4.52 | 5.00 | 5.37 | 5.39 | 5.57 |
| | $C2^-$ | 26.54 | 24.83 | 28.52 | 27.02 | 24.92 | 25.24 | 25.05 |
| | $C3^-$ | 41.81 | 42.35 | 42.98 | 43.24 | 42.04 | 41.67 | 41.63 |
| | $C4^-$ | 17.86 | 19.91 | 18.98 | 18.08 | 18.10 | 18.36 | 18.95 |
| | $C2°-C4°$ | 0.95 | 1.66 | 1.06 | 2.05 | 2.63 | 2.44 | 2.53 |
| | $C5^+$ | 4.43 | 1.49 | 3.02 | 3.36 | 3.35 | 4.29 | 4.92 |

We claim:

1. A method for preparing a ZSM-5 based catalyst adapted to be used in the catalytic conversion of methanol or dimethyl ether to light olefins comprising the following consecutive steps:

mixing a zeolite ZSM-5 with silica sol and ammonium nitrate solution, kneading, moulding, drying and calcining the mixture, exchanging the modified zeolite with a solution of HCl at 70°–90° C., drying and calcining the H-modified zeolite, impregnating the H-modified zeolite with phosphoric acid under reduced pressure, drying and calcining the P-modified zeolite, impregnating the P-modified zeolite with a solution of rare earth elements under reduced pressure, drying and calcining the P-rare earths-modified zeolite, hydrothermally treating the P-rare earths-modified zeolite at 500°–600° C. with water vapour, and calcining the modified zeolite.

2. A method according to claim 1 wherein, in the first step, the ZSM-5 is mixed also with a pore structure regulator selected in the group consisting of sodium carboxy methyl cellulose, activated carbon, Sesbania seeds powder, starch and mixture thereof.

3. A method according to claim 2 wherein, in the first step, the ZSM-5 is mixed with Sesbania seeds powder in an amount comprised between 3 and 10% by weight.

4. A zeolite ZSM-5 based catalyst for the conversion of methanol or dimethyl ether to light olefins containing at least 0.7% by weight of phosphorous and at least 0.97% by weight of rare earth elements and in that it presents an at least bimodal pore size distribution at 35–45 Å and 170–250 Å.

5. A zeolite ZSM-5 based catalyst according to claim 4 wherein it presents an at least bimodal pore size distribution at about 40 Å and 117 Å.

* * * * *

UNITED STATES PATENT AND TRADEMARK OFFICE
CERTIFICATE OF CORRECTION

PATENT NO. : 5,573,990
DATED : November 12, 1996
INVENTOR(S) : Wang Gongwei, Ying Muliang, Wang Xingchun and Chen Guoquan It is certified that error appears in the above-indentified patent and that said Letters Patent is hereby corrected as shown below:

On Title and Information page:

"[75] Inventors: Gongwei Wang; Muliang Ying; Xingchun Wang; Guoquan Chen, all of Dalian, China"

is changed to:

--[75] Inventors: Wang Gongwei; Ying Muliang; Wang Xingchun; Chen Guoquan; all of Dalian, China--.

Signed and Sealed this

Eleventh Day of February, 1997

Attest:

BRUCE LEHMAN

*Attesting Officer*  *Commissioner of Patents and Trademarks*